United States Patent
Arnoldy

(10) Patent No.: US 7,560,605 B2
(45) Date of Patent: Jul. 14, 2009

(54) PROCESS FOR PRODUCING BRANCHED OLEFINS FROM LINEAR OLEFIN/PARAFFIN FEED

(75) Inventor: Peter Arnoldy, Amsterdam (NL)

(73) Assignee: Shell Oil Company, Houston, TX (US)

( * ) Notice: Subject to any disclaimer, the term of this patent is extended or adjusted under 35 U.S.C. 154(b) by 0 days.

(21) Appl. No.: 12/134,811

(22) Filed: Jun. 6, 2008

(65) Prior Publication Data

US 2008/0242748 A1    Oct. 2, 2008

Related U.S. Application Data

(62) Division of application No. 11/540,529, filed on Sep. 28, 2006, now Pat. No. 7,414,161, which is a division of application No. 10/218,732, filed on Aug. 14, 2002, now Pat. No. 7,157,613.

(30) Foreign Application Priority Data

Aug. 17, 2001    (EP) .................................. 01306995

(51) Int. Cl.
*C07C 2/64*    (2006.01)
*C07C 5/27*    (2006.01)

(52) U.S. Cl. .................... 585/323; 585/671; 585/446; 585/448

(58) Field of Classification Search ................ 585/323, 585/671, 446, 448
See application file for complete search history.

(56) References Cited

U.S. PATENT DOCUMENTS

| 3,169,987 | A | * | 2/1965 | Bloch ........................... 562/94 |
| 3,830,870 | A | | 8/1974 | Harter et al. .............. 260/683.2 |
| 4,777,322 | A | | 10/1988 | Hoelderich et al. .......... 585/666 |
| 5,516,959 | A | | 5/1996 | Rahmim et al. ............. 585/671 |
| 5,849,960 | A | | 12/1998 | Singleton et al. ............ 568/909 |
| 6,111,158 | A | | 8/2000 | Marinangeli et al. ......... 585/467 |
| 6,187,981 | B1 | | 2/2001 | Marinangeli et al. ......... 585/323 |
| 7,157,613 | B2 | | 1/2007 | Arnoldy ...................... 585/671 |

FOREIGN PATENT DOCUMENTS

| EP | 0170182 | 2/1986 |
| WO | WO03016249 | 2/2003 |

OTHER PUBLICATIONS

"Petrochemical route to Detergent Intermediates," by B. V. Vora, P. R. Pujado and M. A. Allawala, UOP Inc., Des Plaines, Illinois, USA.
"Upgrading Kerosene to Normal Paraffins," by Anne McPhee, Petrochemicals and Gas Processing, PTW Winter 1999/2000, pp. 127-131.

* cited by examiner

*Primary Examiner*—Thuan Dinh Dang

(57) ABSTRACT

A process for producing branched olefins from a mixed linear olefin/paraffin isomerisation feed comprising linear olefins having at least 7 carbon atoms in 5-50% w comprising in a first stage skeletally isomerising linear olefins in the isomerisation feed and in a second stage separating branched and linear molecules wherein branched molecules are substantially olefinic and linear molecules are olefinic and/or paraffinic; novel stages and combinations thereof; apparatus therefor; use of catalysts and the like therein; and use of branched olefins obtained thereby.

2 Claims, 1 Drawing Sheet

PROCESS FOR PRODUCING BRANCHED OLEFINS FROM LINEAR OLEFIN/PARAFFIN FEED

CROSSREFERENCE TO PRIOR APPLICATION

This application is a divisional application of Ser. No. 11/540,529 filed Sep. 28, 2006 now U.S. Pat. No. 7,414,161, which is a divisional application of 10/218,732 filed Aug. 14, 2002 now U.S. Pat. No. 7,157,613, which claims priority to European Application No. 01306995.0 filed Aug. 17, 2001.

FIELD OF THE INVENTION

The present invention relates to a process for producing branched olefins from a linear olefin/paraffin feed, and apparatus therefor.

BACKGROUND OF THE INVENTION

The derivatives of long chain olefins having about 7 to 28 carbon atoms have considerable commercial importance in a variety of applications, including detergents, surfactants and freeze point depressants in lubricating oils. Primary derivatives which are used in many household laundry detergents include alcohols which are produced by hydroformylation, and alkyl benzenes, for example linear alkyl benzene (LAB) and modified alkylbenzenes (MAB) which are produced by the alkylation of benzene.

In the application to detergents, surfactants and the like, primary derivatives are generally converted to anionic or nonionic detergents or surfactants by sulfonation or ethoxylation, respectively, of the derivative. Important considerations in providing effective detergents or general surfactants is cold water solubility/detergency, which is usually associated with hydrophobic branched olefin precursors, along with the need for good biodegradability which is usually associated with linear olefin precursors. Since these properties are conflicting it is not easily possible to provide surfactants, etc. meeting both requirements.

U.S. Pat. No. 5,849,960 (Shell Oil Company) discloses an alternative solution to this problem by providing a new composition of controlled branching alcohol, and their sulphate derivatives, via the olefin intermediate, in order to decrease hydrophobicity and thereby increase cold water detergency, whilst at the same time exhibiting good biodegradability.

The new compositions of U.S. Pat. No. 5,849,960 are prepared using a process for producing controlled branching primary alcohols from a linear olefin feed in two stages, via their branched olefins. The olefin feed is usually a distribution of at least 50 weight % of linear mono olefins in a specified carbon range, the remainder of the feed being olefin of other carbon number or carbon structure, diolefins, paraffins, aromatics and other impurities, depending on the origin or synthesis process used in providing the feed. The location of the double bond is not limited, the olefin feed composition may comprise alpha-olefins, internal olefins or a mixture thereof. The alkyl branched primary olefins obtained therefrom have from 7 to 35 carbon atoms, and an average number of branches per molecule chain of at least 0.7, containing not only methyl branches but also ethyl branches.

U.S. Pat. No. 6,187,981 (UOP) discloses preparation of modified alkyl benzenes (MAB) and their sulfonates (MABS) by paraffin isomerization and dehydrogenation to olefins, alkylation by olefins of aromatics, and sulfonation. The paraffinic feed for isomerization comprises linear or normal paraffins having a total of 8 to 28 carbon atoms per molecule, and the isomerised stream for dehydrogenation contains a higher concentration of lightly branched paraffins.

SUMMARY OF THE INVENTION

In an embodiment, there is provide a process for producing branched olefins from a mixed linear olefin/paraffin isomerisation feed comprising linear olefins having at least 7 carbon atoms in an amount of 5-50% w comprising: (a) skeletally isomerising linear olefins in the isomerisation feed thereby producing a reaction product stream comprising branched molecules and linear molecules; and (b) separating branched and linear molecules from at least a portion of the reaction product stream wherein branched molecules are substantially olefinic and linear molecules are olefinic and/or paraffinic.

Further there is provided an apparatus for producing branched olefins by means of the process as described above which comprises a first stage catalytic isomerisation unit, a second stage separation unit and feed, product and optional recycle lines and optionally includes a preliminary stage dehydrogenation unit, and recycle line is to the first stage and/or if present to the preliminary stage unit.

DETAILED DESCRIPTION OF THE INVENTION

Figure 1:
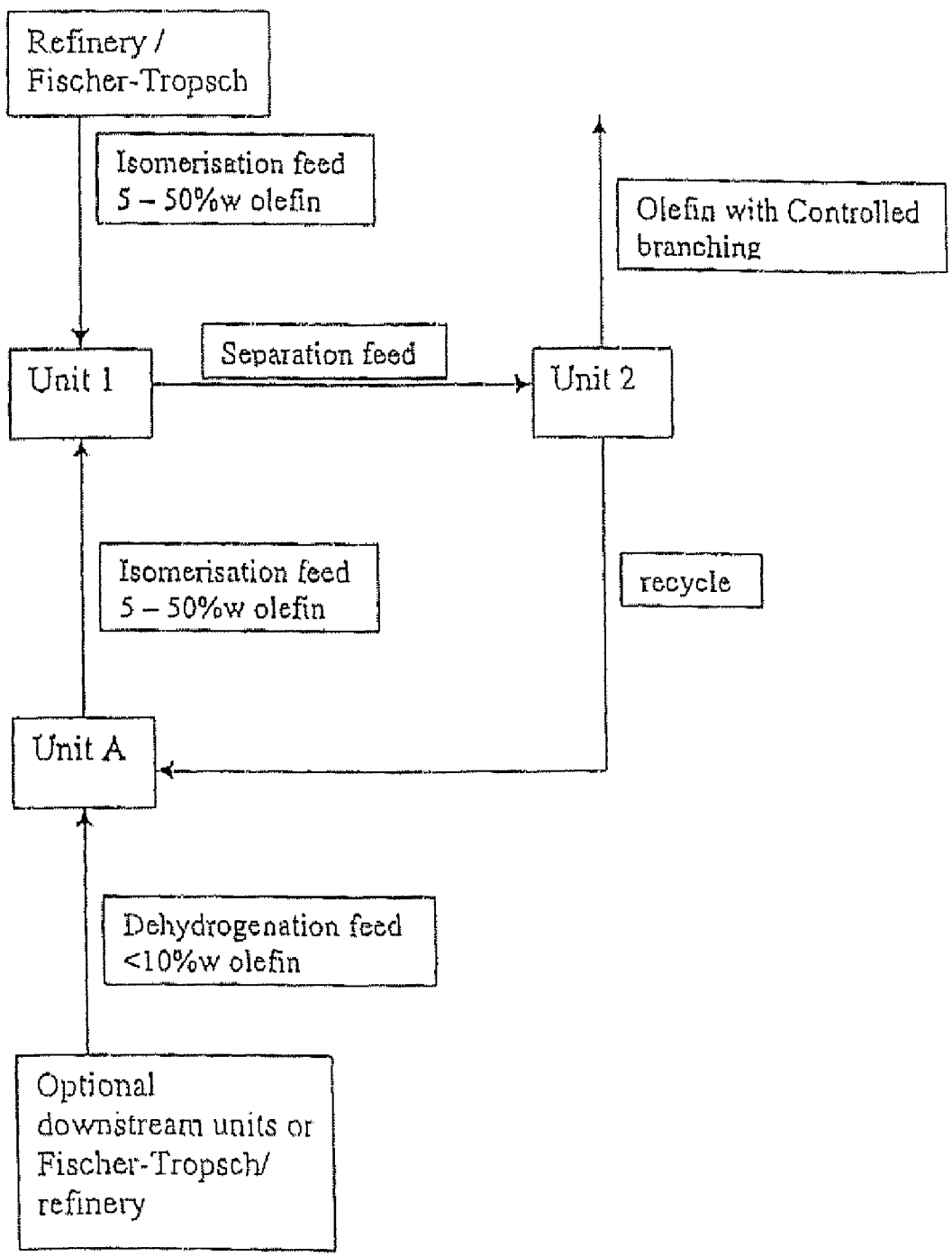
FIG. 1 is a schematic diagram of selected embodiments of a system for producing branched olefins from a mixed linear olefin/paraffin isomerisation feed.

Accordingly, there is provided a process for producing branched olefins from a mixed linear olefin/paraffin isomerisation feed comprising linear olefins having at least 7 carbon atoms in 5-50% w comprising in a first stage skeletally isomerising linear olefins in the isomerisation feed, and in a second stage separating branched and linear molecules wherein branched molecules are substantially olefinic and linear molecules are olefinic and/or paraffinic. More particularly there is provided a process for producing olefins with controlled branching and apparatus therefor.

Preferably the process provides alkyl branched primary olefins having at least 7 carbon atoms, preferably 7 to 28 carbon atoms, more preferably 10 to 16 carbon atoms, and an average number of branches per molecule chain of at least 0.7. Preferably alkyl branches include methyl branches and also some ethyl branches.

Preferably an isomerisation feed comprises 5% to 50% w, for example 10% to 35% w of substantially linear mono olefins having from 7 to 28 carbon atoms, preferably olefins having from 10 to 16 carbon atoms, with the balance being paraffins, olefins of other carbon number or carbon structure, diolefins, aromatics and other impurities, more preferably predominantly paraffins. Suitable feed comprises streams originating from oil refinery processes such as jet fuel or kerosene, or streams originating from Fischer-Tropsch gas to oil facilities.

Optionally the process comprises in a preliminary stage providing an isomerisation feed by dehydrogenation of a substantially linear paraffinic feed for example comprising less than 10% w olefin, or substantially no olefins.

The process may include a recycle from the separation stage to the isomerisation stage or preferably to the preliminary dehydrogenation stage. The recycle may be supplemented by branched olefin/paraffin streams as by-products of downstream units such as light ends from hydroformylation of branched olefins comprising predominantly branched (iso) paraffins.

It is a particular advantage of the present invention that the process may be operated with feed comprising streams from a variety of sources including an isomerisation or dehydrogenation teed having 0% w to 50% w olefin originating from oil refinery processes or Fischer-Tropsch. The process of the invention provides for selective skeletal branching of linear olefins whilst paraffins in the feed remain as unreacted linear paraffins, so enabling simple olefin/paraffin separation with use of known processes for separation of linear and branched molecules. Excellent selectivity is obtained due to minimal byproduct formation, i.e. minimal cracking products and heavy ends.

Skeletal isomerisation of linear olefins may be carried out by any known means. Preferably skeletal isomerisation is with use of the process of U.S. Pat. No. 5,849,960, the contents of which are incorporated herein by reference, with use of a catalytic isomerisation furnace. Preferably an isomerisation feed as hereinbefore defined is contacted with an isomerisation catalyst comprising a catalyst which is effective for skeletal isomerising a linear olefin composition into an olefin composition having an average number of branches per molecule chain of at least 0.7. More preferably the catalyst comprises a zeolite having at least one channel with a crystallographic free channel diameter ranging from greater than 4.2 Angstrom and less than 7 Angstrom, measured at room temperature, with essentially no channel present which has a free channel diameter which is greater than 7 Angstrom. Suitable zeolites are described in U.S. Pat. No. 5,510,306, the contents of which are incorporated herein by reference, and are described in the Atlas of Zeolite Structure Types by W. M. Meter and D. H. Olson. Preferred catalysts include ferrierite, A1PO-31, SAPO-11, SAPO-31, SAPO-41, FU-9, NU-10, NU-23, ZSM-12, ZSM-22, ZSM-23, ZSM-35, ZSM-48, ZSM-50, ZSM-57, SUZ-4A, MeAPO-11, MeAPO-31, MeAPO-41, MeAPSO-11, MeAPSO-31, and MeAPSO-41, MeAPSO-46, ELAPO-11, ELAPO-31, ELAPO-41, ELAPSO-11, ELAPSO-31, and ELAPSO-41, laumontite, cancrinite, offretite, hydrogen form of stilbite, the magnesium or calcium form of mordenite and partheite, and their isotypic structures. Combinations of zeolites can also be used herein. These combinations can include pellets of mixed zeolites and stacked bed arrangements of catalyst such as, for example, ZSM-22 and/or ZSM-23 over ferrierite, ferrierite over ZSM-22 and/or ZSM-23, and ZSM-22 over ZSM-23. The stacked catalysts can be of the same shape and/or size or of different shape and/or size such as ⅛ inch trilobes over 1/32 inch cylinders for example. Alternatively natural zeolites may be altered by ion exchange processes to remove or substitute the alkali or alkaline earth metal, thereby introducing larger channel sizes or reducing larger channel sizes. Such zeolites include natural and synthetic ferrierite (can be orthorhombic or monoclinic), Sr-D, FU-9 (EP B-55,529), ISI-6 (U.S. Pat. No. 4,578,259), NU-23 (E.P.A.-103,981), ZSM-35 (U.S. Pat. No. 4,016,245) and ZSM-38 (U.S. Pat. No. 4,375,573). Most preferably the catalyst is ferrierite.

The skeletal isomerisation catalyst is suitably combined with a refractory oxide as binding material in known manner, for example natural clays, such as bentonite, montmorillonite, attapulgite, and kaolin; alumina; silica; silica-alumina; hydrated alumina; titania; zirconia and mixtures thereof. More preferred binders are aluminas, such as pseudoboehmite, gamma and bayerite aluminas. These binders are readily available commercially and are used to manufacture alumina-based catalysts.

The weight ratio of zeolite to binder material suitably ranges from about 10:90 to about 99.5:0.5, preferably from about 75:25 to about 99:1, more preferably from about 80:20 to about 98:2 and most preferably from about 85:15 to about 95:5 (anhydrous basis).

Preferably skeletal isomerisation is conducted at elevated temperature in the range from about 200° C. to about 500° C., more preferably from about 250 to about 350° C.

Preferably the isomerisation reaction is conducted at pressure ranging from about 0.1 atmospheres (10 kPa) to about 10 atmospheres (1 MPa), more preferably from about 0.5 to about 5 atmospheres (50 to 500 kPa).

The feed to the first stage isomerisation unit comprises linear olefin and more than 50% w paraffin, for example 80-90% w linear paraffin. It is a particular advantage that the feed is readily available as byproducts of downstream units or is prepared in a preliminary stage dehydrogenation facility. In a particular advantage the linear paraffin is thought to act as a diluent in the isomerisation process thereby avoiding heavy ends production.

The catalytic isomerisation conditions are preferably relatively mild conditions whereby an amount of unconverted linear olefin is present in the product stream and is recycled together with linear paraffin, whereby the process may be operated with a high selectivity and low cracking byproduct production. Suitably up to 30% linear olefin is unconverted and is separated in the second stage process and recycled to the first stager more preferably up to 15% w. Preferably the isomerisation is operated in excess of 70% conversion, more preferably in excess of 85% conversion and most preferably in the range 90 to 95% conversion.

The second stage separation of branched olefins from unreacted feed may be by any known process. Preferably separation is via branched/linear separation by contacting the product from the first stage process with a suitable inorganic or organic molecular sieve such as a zeolite of appropriate pore diameter, preferably a 5A zeolite or urea and the like.

The molecular sieve separates molecules by adsorption, with subsequent desorption as known in the art. Suitably separation is via a fixed bed containing adsorbent as defined with separation of a branched olefin stream and recycle of unreacted linear olefin/paraffin stream.

Suitably separation is conducted at elevated temperature in the range of about 100° C. to about 400° C., more preferably from about 180 to about 380° C.

Suitably separation is conducted at pressure ranging from about 2 bar (200 kPa) to about 7 bar (700 kPa).

Suitable unit line up and operation may conveniently employ techniques for example as known in the MOLEX process (UOP) using Sorbex™ separations technology, and a suitable adsorbent may comprise commercially available ADS-14, ADS-34 used in that technology and equivalent adsorbents.

The separation may use feed pretreatment as known in the art to prevent adsorbent poisoning, if required, or this may be achieved in situ in upstream units of the process of the invention.

The preliminary stage dehydrogenation may be by any known means. Preferably dehydrogenation is with use of a standard dehydrogenation facility employing a Pt catalyst, for example PACOL or with use of a dehydrogenation catalyst for example as exemplified in U.S. Pat. Nos. 3,274,287; 3,315,007; 3,315,008; 3,745,112; 4,430,517; 4,716,143; 4,762,960; 4,786,625; and 4,827,072. However, a preferred catalyst comprises a refractory inorganic oxide having uniformly dispersed thereon at least one platinum group (Group VIII (IUPAC 8-10)) metal and at least one promoter metal, for example as disclosed in U.S. Pat. No. 6,187,981. Preferred refractory inorganic oxides include but are not limited to alpha alumina, theta alumina, cordierite, zirconia, titania, and mixtures thereof. When contacting the catalyst, the dehydrogenation feed may be in the liquid phase or in a mixed vapour-liquid phase but preferably in the vapour phase.

The product stream typically comprises linear olefin in 5-50% w, preferably 10 to 35% w, together with unconverted linear paraffin, and forms the isomerisation feed.

Dehydrogenation conditions include a temperature of generally from about 400° C. to about 900° C., preferably from about 400° C. to about 525° C., a pressure of about 1 kPa(g) to about 2000 kPa(g) and a liquid hourly space velocity (LHSV) of from about 0.1 to about 100 $hr^{-1}$.

Feed to the dehydrogenation unit is optionally provided from an oil refinery or Fischer-Tropsch process.

Optionally the process may include additional units for separation of product stream from the linear/branched separation unit, fractionating by molecular weight into for example $C_{10-14}$, $C_{15-16}$ streams and the like.

Optionally the process includes additionally the hydroformylation of product olefin with controlled branching by known means to provide the corresponding alcohol for further conversion to detergents, surfactants and the like; or alkylation of product olefin with controlled branching with benzene by known means to provide the corresponding alkyl benzenes, and optional further sulphonation thereof.

In a further aspect of the invention there is provided a novel process stage or combination thereof as hereinbefore defined.

In a further aspect of the invention there is provided an apparatus for producing branched olefins by means of the process as hereinbefore defined. Suitably the apparatus comprises a first stage catalytic isomerisation unit, a second stage separation unit and product and recycle lines. Optionally the apparatus includes a preliminary stage dehydrogenation unit and recycle line is to the first stage or to the preliminary stage unit. The apparatus includes a feed stream to the first stage unit and/or to the preliminary stage unit.

In a further aspect of the invention there is provided the use of catalysts and the like as hereinbefore defined in the process of the invention as hereinbefore defined.

In a further aspect of the invention there is provided the use of the branched olefins obtained with the process and apparatus of the invention for producing detergents, surfactants, freezing point depressants in lubricating oils and the like. For use in providing soaps, detergents and surfactants the branched olefins of the invention are suitably converted to alcohols by hydroformylation or alkyl benzenes by alkylation and sulphated or ethoxylated by known means.

The invention is now illustrated in non limiting manner with reference to the figures and examples.

FIG. 1 illustrates a schematic of an apparatus of the invention as hereinbefore defined.

In FIG. 1, isomerisation feed (comprising 5% w to 50% w olefin) is fed to Unit 1 which represents a unit for controlled skeletal isomerisation of olefins. Product stream from Unit 1 is fed to Unit 2 which represents a linear/branched separation unit, for example MOLEX (UOP). This unit produces two separated streams, a product stream comprising olefin with controlled branching which is suitable for hydroformylation to alcohol or alkylation to alkyl benzene and subsequent sulfonation or ethoxylation to form commercial detergents, and a recycle stream comprising linear hydrocarbons, mainly paraffins.

The recycle stream from Unit 2 is fed to Unit A which represents a paraffin dehydrogenation to olefins Unit, for example PACOL (UOP). Product stream from Unit A is recycled to Unit 1.

In the FIGURE the isomerisation feed to Unit 1 is derived from oil refinery or Fischer-Tropsch, directly or indirectly via PACOL Unit A. Where feed enters depends on its olefinicity, if a feed comprises 0-10% w olefins it enters at Unit A, if it comprises 5-50% w olefins it enters at Unit 1.

The unit line up is optionally fed with dehydrogenation feed from downstream Units to Unit A, in addition to isomerisation feed comprising 5% w to 50% w olefin to Unit 1.

Unit 1 comprises a catalyst as described in U.S. Pat. No. 5,849,960, Unit 2 comprises a linear/branched separation agent such as urea or molecular sieve, Unit A comprises platinum dehydrogenation catalyst with or without promoter(s).

The product olefin from Unit 2, having controlled branching is suitably separated by molecular weight into streams such as $C_{10-14}$, for conversion for example to MLAB type products, $C_{15-16}$ which is suitable for conversion to branched detergent alcohol and the like.

EXAMPLES

Illustrative examples of typical feed and product streams from processes using the apparatus of FIG. 1 are described in Examples 1 to 3 below and are given in the following Tables 1 to 4.

Example 1

Fresh Feed to Isomerisation Unit

In this example fresh feed is passed to isomerisation Unit 1 only (To U1); product stream is passed to Unit 2 for linear/branched separation (U1/U2); olefin product is obtained from Unit 2 (From U2); unconverted (linear paraffin and any remaining linear olefin) feed is recycled from Unit 2 to dehydrogenation Unit A (U2/UA); and the resultant linear olefins from Unit A are passed back to Unit 1 for isomerisation (UA/U1).

The olefin product from the Example is shown in column 5 (From U2) and represents 100% conversion to branched olefin.

TABLE 1

| Model Mass Balance using arbitrary flow units, for case with fresh feed to Unit 1 | | | | | |
|---|---|---|---|---|---|
| | To U1 | To UA | U1/U2 | From U2 | U2/UA | UA/U1 |
| Linear olefin | 30 | 0 | 11 | 0 | 11 | 81 |
| Branched olefin | 0 | 0 | 100 | 100 | 0 | 0 |
| Linear paraffin | 70 | 0 | 800 | 0 | 800 | 730 |

Example 2

Fresh Feed to Dehydrogenation Unit

In this example fresh feed is passed to dehydrogenation Unit A only (To UA); product of dehydrogenation Unit A is passed to Unit 1 (UA/U1); product stream of Unit 1 is passed to Unit 2 for linear/branched separation (U1/U2); olefin product is obtained from Unit 2 (From U2); unconverted (linear paraffin and any remaining linear olefin) feed is recycled from Unit 2 to dehydrogenation Unit A (U2/UA); and the resultant linear olefins from Unit A are passed back to Unit 1 for isomerisation (UA/U1).

The olefin product from the Example is shown in column 5 (From U2) and represents 100% conversion to branched olefin.

TABLE 2

Model Mass Balance using arbitrary flow units, for case with fresh feed to Unit A

|  | To U1 | To UA | U1/U2 | From U2 | U2/UA | UA/U1 |
|---|---|---|---|---|---|---|
| Linear olefin | 0 | 0 | 11 | 0 | 11 | 111 |
| Branched olefin | 0 | 0 | 100 | 100 | 0 | 0 |
| Linear paraffin | 0 | 100 | 1000 | 0 | 1000 | 1000 |

Example 3

This example illustrates a method of preparation of a catalyst useful for isomerising linear olefins to branched olefins. An ammonium-ferrierite having a molar silica to alumina ratio of 62:1, a surface area of 369 square meters per gram (P/Po=0.03), a soda content of 480 ppm and n-hexane sorption capacity of 7.3 g per 100 g of zeolite was used as the starting zeolite.

The catalyst components were mulled using a Lancaster mix muller. The mulled catalyst material was extruded using a 1 inch or a 2.25 inch Bonnot pin barrel extruder.

The binder utilized was CATAPAL® D, F4M hydroxypropyl methylcellulose from The Dow Chemical Company was used as an extrusion aid. The acids were obtained from The Aldrich Chemical Company.

Isomerisation Catalyst Preparation

The Lancaster mix muller was loaded with 645 grams of ammonium-ferrierite (5.4% loss on ignition ("LOI")) and 91 grams of CATAPAL® D alumina (LOI of 25.7%). The alumina was blended with the ferrierite for 5 minutes during which time 152 milliliters of deionized water was added. A mixture of 6.8 grams glacial acetic acid, 7.0 grams of citric acid and 152 milliliters of deionized water was added slowly to the muller in order to peptize the alumina. The mixture was mulled for 10 minutes. 0.20 grams of tetraamine palladium nitrate in 153 grams of deionized water were then added slowly as the mixture was mulled for a period of 15 additional minutes. The extrusion mix had an LOI of 43.5%. The 90:10 zeolite/alumina mixture was transferred to the 2.25 inch Bonnot extruder and extruded using a stainless steel die plate with $\frac{1}{16}$" holes.

The moist extrudate was dried at 125° C. for 16 hours. After drying, the extrudate was longsbroken manually. The extrudate was calcined in flowing air at 200° C. for two hours and at a maximum temperature of 500° C. for two hours. The extrudate was allowed to cool in a nitrogen filled dessicator before loading into the reactors.

Testing Procedure

Isomerisation

A stainless steel tube, 1 inch OD, 0.6 inch ID and 26 inches long was used as a reactor. A thermowell extended 20 inches from the top of the tube. To load the reactor it was first inverted and a small plug of glass wool was slid down the reactor tube over the thermowell until it hit the bottom of the tube. Silicon carbide (20 mesh) was added to a depth of about 6 inches. Over this was placed a small plug of glass wool. Approximately 6 grams of catalyst particles, 6-20 mesh admixed with about 45 grams of fresh silicon carbide (60-80 mesh) were added in two parts to distribute the catalyst evenly. The catalyst bed was typically about 10 inches long. Another piece of glass wool was added to the top of the catalyst and the reactor was topped with 20 mesh silicon carbide, followed by a final plug of glass wool. A multipoint thermocouple was inserted into the thermowell and was positioned such that the temperature above, below and at three different places in the catalyst bed could be monitored. The reactor was inverted and installed in the furnace.

The isomerisation feed utilized was obtained from a Fischer-Tropsch reaction of carbon monoxide and hydrogen which yielded a mixture of primary linear paraffins and olefins with some minor amounts of dienes and oxygenates present in it. The mixture was fractionated by distillation into various boiling cuts. The composition of the isomerisation feed used is shown in Table 3 below. The isomerisation feed was vaporised before contacting the isomerisation catalyst.

To start up the reactor, it was first heated to the desired operating temperature over a four hour period and held at the operating temperature for 2 hours, all under flowing nitrogen. 60 g/hr of isomerisation feed was pumped to the reactor. 6 l/hr of nitrogen was also passed over the catalyst with the feed simultaneously. The reactor was operated at an outlet pressure of 20 kPa above atmospheric pressure and a temperature of 280° C. Lower temperatures can be used at lower feed rates and if the amount of alcohol present in the feed is lower. For example, greater than 90% of the linear olefins are converted to branched olefins at 230° C. when the oxygenates in the feed are removed first from the feed before it is isomerised. Higher temperatures can be used at higher feed rates.

Table 3 below shows the composition of the isomerisation feed used in Example 3, analysed by gas chromatography. Table 4 shows the wt % of C8-C10 branched olefins, C8-C10 linear olefins and C8-C10 paraffins in the isomerisation feed (after 0 hours) and in the effluent (after 24 and 48 hours of isomerisation).

TABLE 3

Isomerisation Feed

| Type of hydrocarbon in feed | Wt % in feed |
|---|---|
| C7 and lighter hydrocarbons | 0.12 |
| C8 branched olefins | 0.02 |
| C8 linear olefins | 0.75 |
| 1-Octene | 0.69 |
| n-Octane | 2.21 |
| C9 branched olefins | 0.16 |
| C9 linear olefins | 8.52 |
| 1-Nonene | 8.07 |
| n-Nonane | 20.03 |
| C10 branched olefins | 0.28 |
| C10 linear olefins | 22.92 |
| 1-Decene | 20.87 |
| n-Decane | 41.12 |
| C11 and heavier hydrocarbons | 0.21 |
| C9-C11 alcohols | 3.56 |

TABLE 4

Wt % of C8-C10 branched olefins, C8-C10 linear olefins and C8-C10 paraffins in isomerisation feed (after 0 hours) and in effluent (after 24 and 48 hours)

| Time on Stream (Hrs) | 0 (Feed) | 24 Hr. | 48 Hr. |
|---|---|---|---|
| C8-C10 branched olefins | 0.46 (wt %) | 33.04 (wt %) | 33.16 (wt %) |
| C8-C10 linear olefins | 32.19 (wt %) | 2.52 (wt %) | 2.54 (wt %) |

TABLE 4-continued

Wt % of C8-C10 branched olefins, C8-C10 linear olefins and C8-C10 paraffins in isomerisation feed (after 0 hours) and in effluent (after 24 and 48 hours)

| Time on Stream (Hrs) | 0 (Feed) | 24 Hr. | 48 Hr. |
|---|---|---|---|
| C8-C10 paraffins | 63.19 (wt %) | 63.32 (wt %) | 63.27 (wt %) |
| Branched to linear C8-C10 olefins ratio | 0.1 (wt %) | 13.1 (wt %) | 13.1 (wt %) |

The results in Table 4 show that the majority of linear olefins were converted into branched olefins during the isomerisation step. During the isomerisation step a small amount of material boiling below C8 was generated from cracking side reactions. In addition, a portion of the C9-C11 alcohols present in the feed were dehydrated to yield additional olefins in the product. The average number of alkyl branches on the C8-C10 olefins in the product was 1.0.

I claim:

1. A process for producing alkyl benzenes from a mixed linear olefin/paraffin isomerization feed comprising linear olefins having at least seven carbon atoms in an amount of 5-50% w consisting of:
   (a) skeletally isomerizing linear olefins in the isomerization feed thereby producing a reaction product stream comprising branched molecules and linear molecules;
   (b) separating branched and linear molecules from at least a portion of the reaction product stream wherein the branched molecules are substantially olefinic and the linear molecules are olefinic and/or paraffinic; and
   (c) alkylating the branched olefins with controlled branching with benzene to the corresponding alkyl benzenes; and
   (d) optionally, sulfonating the alkyl benzenes.

2. A process for producing alkyl benzenes from a mixed linear olefin/paraffin isomerization feed comprising linear olefins having at least seven carbon atoms in an amount of 5-50% w consisting of:
   (a) skeletally isomerizing linear olefins in the isomerization feed thereby producing a reaction product stream comprising branched molecules and linear molecules;
   (b) separating branched and linear molecules from at least a portion of the reaction product stream wherein the branched molecules are substantially olefinic and the linear molecules are olefinic and/or paraffinic, wherein the linear molecules are recycled to step (a); and
   (c) alkylating the branched olefins with controlled branching with benzene to corresponding alkyl benzenes.

* * * * *